(12) United States Patent
Westerhof et al.

(10) Patent No.: US 12,220,217 B2
(45) Date of Patent: Feb. 11, 2025

(54) DEVICE, SYSTEM AND METHOD FOR MEASUREMENT OF A SKIN PARAMETER

(71) Applicant: KONINKLIJKE PHILIPS N.V., Eindhoven (NL)

(72) Inventors: Willem Auke Westerhof, Drachten (NL); Yue Wu, Amsterdam (NL); Sahil Wadhwa, Venlo (NL); Willem Minkes, Emmeloord (NL); Nicole Louisa De Klein, Amsterdam (NL); Martijn Van Zutphen, Marum (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 956 days.

(21) Appl. No.: 16/977,620

(22) PCT Filed: Feb. 27, 2019

(86) PCT No.: PCT/EP2019/054885
§ 371 (c)(1),
(2) Date: Sep. 2, 2020

(87) PCT Pub. No.: WO2019/170497
PCT Pub. Date: Sep. 12, 2019

(65) Prior Publication Data
US 2020/0390362 A1    Dec. 17, 2020

(30) Foreign Application Priority Data
Mar. 7, 2018  (EP) ..................................... 18160454

(51) Int. Cl.
*A61B 5/0531*    (2021.01)
*A61B 5/00*      (2006.01)
*A61B 5/0537*    (2021.01)

(52) U.S. Cl.
CPC .......... *A61B 5/0531* (2013.01); *A61B 5/0053* (2013.01); *A61B 5/0077* (2013.01);
(Continued)

(58) Field of Classification Search
CPC ... A61B 5/0531; A61B 5/0053; A61B 5/0077; A61B 5/0537; A61B 5/442;
(Continued)

(56) References Cited

U.S. PATENT DOCUMENTS

| 6,122,544 A  * | 9/2000 | Organ ................... A61B 5/0531 |
| | | 600/547 |
| 6,591,122 B2 * | 7/2003 | Schmitt ................ A61B 5/0059 |
| | | 600/310 |

(Continued)

FOREIGN PATENT DOCUMENTS

| CN | 201624959 | 11/2010 |
| CN | 204542063 | 8/2015 |

(Continued)

OTHER PUBLICATIONS

International Search Report and Written Opinion Dated Jun. 11, 2019 For International Application No. PCT/EP2019/054885 Filed Feb. 27, 2019.

(Continued)

*Primary Examiner* — Yi-Shan Yang
*Assistant Examiner* — Kyle W. Kretzer

(57) ABSTRACT

The present invention relates to a device for skin parameter measurement, comprising a housing structure (112) defining an interior cavity (120) and a first opening (122) at a skin contact end (124) of the interior cavity (120), a movable part (113, 117) connected to the housing structure (112) via an elastic connecting arrangement (126), the movable part (113, 117) being movable with respect to the housing structure (112) and configured to protrude the skin contact end (124)

(Continued)

through the first opening (122) of the housing structure when no external force is applied to move the movable part (113, 117) with respect to the housing structure, the movable part (113, 117) further comprising a second opening (116), an optical sensing unit (118) for performing measurement of a first skin parameter when the device is in contact with a skin surface, the optical sensing unit being provided within the interior cavity of the housing structure and comprising an illuminating unit (118A) for illuminating the skin surface by emitting light through the second opening (116) of the movable part and an imaging unit (118B) for receiving light reflected by the illuminated skin surface, and an electrical sensing unit (136) for measuring a second skin parameter, wherein the electrical sensing unit (136) is arranged at a front end section of the movable part (113, 117) defining the second opening (116).

20 Claims, 8 Drawing Sheets

(52) U.S. Cl.
CPC ............ *A61B 5/0537* (2013.01); *A61B 5/442* (2013.01); *A61B 5/6843* (2013.01); *A61B 2562/0233* (2013.01)

(58) Field of Classification Search
CPC .......... A61B 5/6843; A61B 2562/0233; A61B 5/441; A61B 5/443
See application file for complete search history.

(56) References Cited

U.S. PATENT DOCUMENTS

| | | | |
|---|---|---|---|
| 6,847,835 B1* | 1/2005 | Yamanishi | A61B 5/443 |
| | | | 600/315 |
| 2004/0257439 A1* | 12/2004 | Shirai | A61B 5/0059 |
| | | | 348/61 |
| 2007/0185392 A1* | 8/2007 | Sherman | A61B 5/0531 |
| | | | 600/372 |
| 2008/0033315 A1* | 2/2008 | Kim | A61B 5/442 |
| | | | 600/547 |
| 2016/0128605 A1 | 5/2016 | Moreno | |
| 2016/0310023 A1* | 10/2016 | Chachisvilis | A61B 5/0053 |
| 2018/0042683 A1 | 2/2018 | Cohen | |
| 2019/0125249 A1* | 5/2019 | Rattner | A61B 5/443 |

FOREIGN PATENT DOCUMENTS

| | | |
|---|---|---|
| DE | 4242083 | 7/1995 |
| EP | 2552311 | 2/2013 |
| GB | 2132483 | 7/1984 |
| JP | H09253066 | 9/1997 |
| JP | H10272112 | 10/1998 |
| JP | H1176172 | 3/1999 |
| WO | 2014/029509 | 2/2014 |
| WO | 2014155782 | 10/2014 |
| WO | 2018/029286 | 2/2018 |
| WO | WO-2018029286 A1 * | 2/2018 ........... A61B 5/0053 |

OTHER PUBLICATIONS

International Preliminary Report on Patentability Dated Jan. 10, 2020 For International Application No. PCT/EP2019/054885 Filed Feb. 27, 2019.

le;2.5qLinda D. Rhein, et al: "Surfactants in Personal Care Products and Decorative Cosmetics", Third Edition, 2006, Section 3.3.3.2 Nova DPM 9003.

* cited by examiner

| device number | Floating rim thickness [mm] | Floating rim shape | Floating rim thickness [mm] |
|---|---|---|---|
| 1 | 2 | flat | 2 |
| 2 | 3 | flat | 0 |
| 3 | 3 | round | 4 |
| 4 | 2 | round | 2 |
| 5 | 1 | round | 0 |
| 6 | 1 | flat | 4 |
| 7 | 3 | flat | 3 |
| 8 | 3 | flat | 2 |

# DEVICE, SYSTEM AND METHOD FOR MEASUREMENT OF A SKIN PARAMETER

CROSS REFERENCE TO RELATED APPLICATIONS

This application is the U.S. National Phase application under 35 U.S.C. § 371 of International Application No. PCT/EP2019/054885 filed Feb. 27, 2019, which claims the benefit of European Patent Application Number 18160454.7 filed Mar. 7, 2018. These applications are hereby incorporated by reference herein.

FIELD OF THE INVENTION

The present invention relates to a device, system and method for measurement of a skin parameter.

BACKGROUND OF THE INVENTION

Measurements of skin parameters provide information related to the skin condition, i.e. the oiliness, the hydration level, the texture, the distribution and appearance of pores, the color and the pigmentation of human skin. Based on such information, personalization of skincare systems (i.e. shaver and cleansing systems) can be achieved by adapting the settings of such systems to personal needs. Further, it is also possible to provide personalized coaching and guidance on skincare measures, skin-related routines, lifestyles and improvements of environmental conditions, i.e. by enabling coaching software applications ("coaching apps") to be used with communication devices such as smartphones or tablet computers.

Skin parameter measurement devices measure skin oiliness and other skin parameters such as skin texture and pores. Some devices in consumer, professional and semi-professional spheres use a camera to acquire images and then utilize image processing algorithms to measure human skin parameters.

However, the skin parameter measurement devices known in the art suffer from variation of measurement results due to the variation of image acquisition conditions. In particular, when taking the image of the same spot on the skin of the same user repeatedly, even without delays between the measurements, the resulting images may greatly vary in the appearance of the imaged skin spot. One of the primary causes for such variations is skin doming, i.e. the dome-like deformation of the skin that occurs when the rigid housing frame of the device is pressed against the skin surface which is elastic.

The effect of skin doming may be even affected in its extent and properties by a number of factors including natural skin properties (e.g. of a person) such as the elasticity, properties of the supporting tissues beneath the skin (e.g. muscle, bone), the design and/or dimensions of the rigid housing frame that is pushed against the skin surface for measurements of a skin parameter, and the pressure level and force with which the rigid housing frame is pushed.

The natural skin properties of a person cannot be controlled by product design measures. However, they are fairly stable in time for the same person on the same skin location. Though being partially extractable from the skin parameter measurement results regarding a particular skin location, the natural skin properties are not a primary factor for variations of skin parameter measurement results regarding that particular skin location.

In addition, the dimensions of the rigid housing frame of skin parameter measurement devices are strongly limited, especially by specific product requirements. Nevertheless, the housing frame may be designed to reduce variations in the profile and extent of the skin doming to a certain degree.

However, the last of the above-mentioned factors, i.e. the pressure level and force, has the largest effect on the skin doming and thus the variations of skin parameter measurement results. The force, with which the skin parameter measurement device is pressed against the skin may strongly vary, leading to variations of skin doming. For instance, a volunteer test shows that the range of forces applied by a group of test persons when asked to "make contact gently on the forehead or cheek" can be as large as from zero to 15 N.

JPH09253066A discloses a pressure stable probe for digitally measuring a treating effect by a magnetic treatment and a blood circulation measuring device using the probe. The pressure stable probe is composed of a cylindrical probe case, a probe electrode incorporated in the case and made slidable in an axial direction inside the case and a pressure distribution body attached to the tip part of the probe case for distributing pressurizing force applied to the probe electrode.

WO 2018/029286 A1 discloses a device comprising a means for attaching the device to an image recording device and a mechanical means configured for applying a pre-defined pressure to skin such that skin is deformed under the pre-defined pressure. The mechanical means is adapted such that an image of the deformed skin can be recorded by the image recording device when the device is attached to the image recording device. Further, a system and a method for determining skin elasticity are presented.

SUMMARY OF THE INVENTION

It is an object of the present invention to provide a device, system and method for skin parameter measurement which enable reducing the variations of skin parameter measurement results, in particular by minimizing the skin doming effect during skin parameter measurements.

In a first aspect of the present invention a device for skin parameter measurement is presented that comprises a housing structure defining an interior cavity and a first opening at a skin contact end of the interior cavity, a movable part connected to the housing structure via an elastic connecting arrangement, the movable part being movable with respect to the housing structure such that the movable part at least partly remains within the housing structure and configured to protrude from the first opening when no external force is applied to the movable part, the movable part further comprising a second opening at a front end section, an optical sensing unit for performing measurement of a first skin parameter, the optical sensing unit being provided within the interior cavity of the housing structure and comprising an illuminating unit for illuminating the skin surface by emitting light through the second opening of the movable part and an imaging unit for receiving light reflected by the illuminated skin surface, and an electrical sensing unit for measuring a second skin parameter, wherein the electrical sensing unit is arranged at a front end section of the movable part defining the second opening.

In a further aspect of the present invention a skincare system is presented that comprises a device for skin parameter measurement as disclosed herein and an analysis unit for analyzing a measurement result provided by the device.

The skincare system may further comprise an adaptation unit for adapting a setting of the system based on an analysis result of the analysis unit.

In a further aspect of the present invention a method for skin parameter measurement using a device as disclosed herein is presented that comprises the steps of performing, using the optical sensing unit, measurement of a first skin parameter when the device is in contact with a skin surface, illuminating, using the illuminating unit, the skin surface by emitting light through the second opening of the movable part, receiving, using the imaging unit, light reflected by the illuminated skin surface, and performing, using the electrical sensing unit, measurement of a second skin parameter when the device is in contact with a skin surface.

In yet further aspects of the present invention, there are provided a computer program which comprises program code means for causing a computer to perform the steps of the method disclosed herein when the computer program is carried out on a computer as well as non-transitory computer-readable recording medium that stores therein a computer program product, which, when executed by a device, causes the method disclosed herein to be performed.

Preferred embodiments of the invention are defined in the dependent claims. It shall be understood that the claimed system, method and computer program have similar and/or identical preferred embodiments as the claimed device and as defined in the dependent claims.

The housing structure of the skin parameter measurement device defines a longitudinal direction. The skin contact end is one of both ends along the longitudinal direction that is closer to the skin surface than the other end when performing the skin parameter measurement. The housing structure may have a cylindrical form defining a cylindrical hollow space (i.e. the interior cavity).

By means of the elastic connecting arrangement, the movable part is movable with respect to the housing structure. In particular, due to the elasticity of the connecting arrangement, the movable part is constantly force-biased to protrude the housing structure at its skin contact end via the first opening when no external force is applied to move the movable part (e.g. before the device is brought into contact with the skin surface), i.e. the movable part is in an unpressed state. The "external force" here means any mechanical force that does not originate from the device itself but applied from an external entity (such as pressing force against the skin).

The elastic connecting arrangement may comprise one or more springs, preferably contraction springs. Further preferably, the springs are pretensioned before integration into the skin parameter measurement device of the present invention. Other examples of the elastic connecting arrangement include, but are not limited to, elastic membrane, rubber, form memory materials such as memory foam.

The second opening is arranged at the front end section of the movable part which protrudes the first opening in the unpressed state and first touches the skin surface when the device is brought into contact with the skin. When during skin parameter measurement the device is brought to contact the skin surface, the front end section of the movable part first contacts the skin surface. When the device is pressed further towards the skin surface, the skin surface exerts a pressure force which moves the movable part inwards towards the interior cavity of the housing structure. This lasts under ongoing pressing of the device towards the skin until the skin contact end of the housing structure which surrounds the movable part is also in contact with the skin surface.

In this way, the movable part constitutes a "floating frame" that is not fixed to the rigid housing structure ("rigid frame") but is movable with respect to the latter.

The optical sensing unit is adapted to measure one or more skin parameters such as oiliness, hydration, texture, pores, color and pigmentation of human skin. The illuminating unit is arranged within the interior cavity of the housing structure in such a way that light (such as visible light or light outside the visible optical spectrum, in particular infrared or ultraviolet) emitted by the illuminating unit reaches the skin surface in proximity to or in contact with the device, in particular the movable part, via the second opening of the movable part. The imaging unit comprises preferably a camera, for instance a CCD camera, or an optoelectronic imaging sensor.

Using the movable part as a floating frame movable relative to the housing structure, the force with which the device presses against the user skin is not limited by the level of the pressing force, but by the elastic force (e.g. the spring compression force) of the elastic connecting arrangement at a given relative position between the movable part and the housing structure. The elastic force is primarily determined by the characteristics of the elastic connecting arrangement itself, so that it is reasonably controllable to at least reduce the force variation to a minimum level. For instance, when utilizing one or more springs for the elastic connecting arrangement, the length and/or stiffness (i.e. spring constant) can be chosen to minimize the spring compression force variation.

The above-mentioned negative effects caused by variations of the pressing force applied by the same or different users of the skin parameter measurement device when measuring the same skin spot are therefore compensated by the better controllable elastic force. In particular, the present invention results in a reduced variation of the skin doming, in particular the height of the skin domes.

Besides reduced doming variations, the resulting doming itself is also reduced compared to the case of a device without such a floating frame. This, in turn, improves lowering the variation in visual skin properties due to variation in the way different users press the device to their skin for measurement and even in the way the same user presses with different strengths in different measurement occasions. The lowered doming profile or height also ensures that images of skin parameter measurements are obtained in focus even with an imaging unit providing a relatively small depth of field (e.g. less than 2.5 mm). Thus, measurement results based on image acquisition with the present invention have less variation and are therefore more reliable for skin analysis.

The device further comprises an electrical sensing unit for measuring a second skin parameter, preferably a skin impedance. The electrical sensing unit is thus preferably an impedance sensing unit (e.g. a bio-impedance sensing unit). Skin impedance measurement provides information indicative of skin parameters such as the water content (hydration, sebum content and the salt content. The present invention hence enables a single device that is capable of both optical skin parameter measurement and electrical skin parameter measurement (e.g. skin impedance). The resulting skin parameter measurement device is more compact and cost-efficient, wherein the ergonomic properties of the device can be optimized.

The electrical sensing unit is arranged at a front end section of the movable part defining the second opening. The electrical sensing unit may thus be embedded in the moving part and does not occupy any additional space in or on the device.

In particular, the contact pressure for skin impedance measurement is also better controlled by using the movable part as floating frame so that pressure-related variations of the skin impedance measurement results are significantly reduced. This effect is particularly improved when the electrical sensing unit is arranged at a front end section of the movable part defining the second opening. In this way, the inner circumference of the ring shape of the front end section forms the second opening.

In a preferable embodiment, the front end section of the movable part is configured to be ring-shaped, preferably to have a circular, rectangular or triangular ring shape. In this way, the contact pressure between the movable part (hence the skin parameter measurement device) and the skin surface of the user has a more homogeneous pressure force distribution, which is advantageous for achieving contact pressures within a range suitable for skin impedance measurements. The "ring shape" within the scope of the present invention is not limited to a circular ring shape, but includes also other ring forms such as a rectangular, triangular, hexagonal or octahedral ring shape or a ring shape with an irregularly formed circumference.

Preferably, the ring diameter of the ring shape and/or the diameter of the second opening is within the range of 10-50 mm, more preferably within the range of 15-20 mm. In this way, the ring shape and/or the second opening of the movable part is wide enough to ensure proper feedback of correct placement of the device to the operator/user when the device is placed on the skin.

Further preferably, at least the outer circumference of the ring shape, or alternatively both the outer and the inner circumferences of the ring shape are circular, rectangular or triangular. For instance, the outer circumference of the ring shape may be triangular, while the inner circumference of the ring shape may be circular or rectangular.

In a further preferable embodiment, the electrical sensing unit comprises a plurality of electrical contacts separated from each other and/or distributed within the front end section of the movable part. In this way, electrodes suitable for the electrical skin parameter measurement, e.g. skin impedance measurement, are provided. The distribution of the electrical contacts along the ring shape enables a more reliable skin impedance result since more parts of the skin can be contacted by the electrodes. Alternatively, the electrical contacts may be arranged to form an array of contacts.

In a further preferable embodiment, the electrical sensing unit comprises two electrical contacts, each of the electrical contacts being provided within one of two semi-ring sections of the front end section of the movable part. This enables two electrodes for skin impedance measurement, wherein each of the electrodes takes the form of a semi-ring, preferably a semi-circular arc. The term "semi-ring" is not limited to the case where each electrode covers exactly half of the ring shape (i.e. the circular angle is 180 degree). Each of the semi-ring sections (e.g. circular, rectangular or triangular) may correspond to a circular angle of less than 180 degree, wherein the electrodes are preferably separated e.g. by isolating materials.

In a further preferable embodiment, the illuminating unit is arranged on an illumination circuit board fixedly arranged within the interior cavity of the housing structure and/or the illuminating unit comprises an LED-arrangement including a plurality of LEDs. The illumination circuit board, preferably a printed circuit board (PCB), is stationary with respect to the housing structure and enables an easier, more compact and cost-efficient integration of the illuminating unit into the skin parameter measurement device. The utilization of LEDs renders the present invention more energy-efficient while facilitating the controlling of the illumination. A polarizer may be fixedly arranged on the PCB, such as on the side of the PCB facing the second opening of the movable part.

In a further preferable embodiment, the illumination circuit board comprises a ring form with a circuit board opening for transmission of light to the imaging unit and/or the plurality of LEDs are circumferentially arranged. The circuit board is thus adapted to facilitate the optical measurement of skin parameters. The LEDs enable more homogeneous illumination of the skin surface during the skin parameter measurement.

In a further preferable embodiment, the elastic connecting arrangement comprises at least one spring, preferably two springs, wherein the at least one spring comprises further preferably a contraction spring. In this way, the integration of the movable part into the housing structure is more reliable and cost-efficient, while enabling a compact device.

In a further preferable embodiment, each of the two springs comprises a pretensioned spring having a pretension of preferably 0.55 N. The pretension of the spring, preferably the contraction spring, facilitates that the movable part is pressed in direction of the exterior of the housing structure so as to penetrate the housing structure at the skin contact end via the first opening. For instance, the natural length of the spring may be 18.7 mm, while the spring is contracted by 7.4 mm when being integrated into the skin parameter measurement device as the elastic connecting arrangement, thereby giving rise to a pretension of 0.55 N. Other values for the spring pretension and/or spring stiffness may also be used.

In particular, spring pretension values from 0.3 N to 1.5 N are preferred in order to enable contact between the skin parameter measurement device and the skin surface during skin parameter measurement. Using spring pretension values equal to or higher than 0.3 N, a "straight guide mechanism" (i.e. the movable part being in contact with the skin surface while the housing structure is being pushed towards the skin surface and thereby guided by the movable part) is realised without additional means for preventing "stick slip" (i.e. internal friction in the mechanism, e.g. the straight guide of the moveable part) which may occur for spring pretension values lower than 0.3 N. Using spring pretension values equal to or lower than 1.5 N, the pressing of the skin parameter measurement device on the skin is faciliated by limiting the pressing force necessary to overcome the spring contraction force.

The spring stiffness value is preferably chosen such that the pressing force needed to overcome the spring contraction force in order to enable the "use position" (see e.g. FIG. 5B) remains below the level of the pretension. Also, the spring stiffness is preferably chosen such that the force necessary for maintaining the "use position" is not more than 1.5 N, more preferably not more than 0.8 N. A desirable range for the spring stiffness value is 0 to 0.5 N/mm. The spring stiffness value of zero may be achieved using an electromagnetic actuator.

Further preferably, the movable part ("floating frame") is configured to move inwards by a distance of 3.5 mm when the skin parameter measurement device is pressed against the skin surface until the housing structure ("rigid frame") which surrounds the movable part touches the skin surface. In this state of application, an end interface of the front end section of the movable part is also in contact with the skin surface simultaneously to a base surface of the housing structure, wherein the end interface is positioned by approx. 1 mm inwards compared to the base surface due to the convex curvature of the skin surface (e.g. forehead or cheek of a person). The value of the inward position of the end interface compared to the base surface may vary depending on circumstances such as skin properties, the location where the device is placed, etc.

In a further preferable embodiment, the movable part comprises at least one, preferably two supporting elements each for carrying one of the two springs. In this way, the springs are guided in a direction defined by the supporting elements so that the spring force is better controllable in its direction. The supporting elements may be configured to hold wirings of the device (e.g. wirings for the illuminating unit and/or the imaging unit).

In a further preferable embodiment, the at least one supporting element comprises a guiding leg arranged to penetrate a corresponding guiding hole fixedly provided within the interior cavity of the housing structure. Exemplarily, the guiding hole may be formed in a guiding board that is an integrated part of the device or a separate unit, preferably a circuit board. The guiding board is preferably fixed to the inner wall of the housing structure so that the springs are carried reliably giving rise to better controllable spring forces. The guiding legs are provided to go through the inner space of the springs so that the springs are carried in a secure manner.

The circuit board may be the same as the illumination circuit board so that this incorporates both the function of guiding the movable part and the function of providing circuitry for the illuminating unit. Alternatively, the guiding board may be a separate board, preferably made of plastics.

In a further preferable embodiment, the illuminating unit and/or the imaging unit are fixedly arranged within the movable part. In this way, the illuminating unit and/or the imaging unit are stationary with respect to the movable part. The requirements regarding optical properties of the optical sensing unit (e.g. the field of focus of the imaging unit, such as camera) are determined by the movable part itself, in particular the size/diameter of the (ring-shaped) front end section and/or the position of the illumination/imaging unit with respect to the movable part, regardless of the position of the movable part with respect to the housing structure functioning as external rigid frame.

In a further preferable embodiment, the skin contact end of the housing structure comprises a ring-shaped base surface defining the first opening, the ring-shaped base surface having a ring width of preferably 2 mm or larger. This ensures a stable base for skin contact. The base surface is preferably a flat surface so that the stability is even improved.

In a further preferable embodiment, the skin parameter measurement device further comprises a triggering unit for detecting a relative position of the movable part and/or the electrical contacts with respect to the housing structure in order to trigger a measurement when a predefined relative position is detected. Alternatively, the triggering unit may be configured to detect the impedance value and trigger signalling that a measurement is correctly performed when an impedance value above a lower threshold is detected within a predefined time duration after a start operation by the user.

In a further preferable embodiment, the optical path of the camera is smaller or equal to 60 mm.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
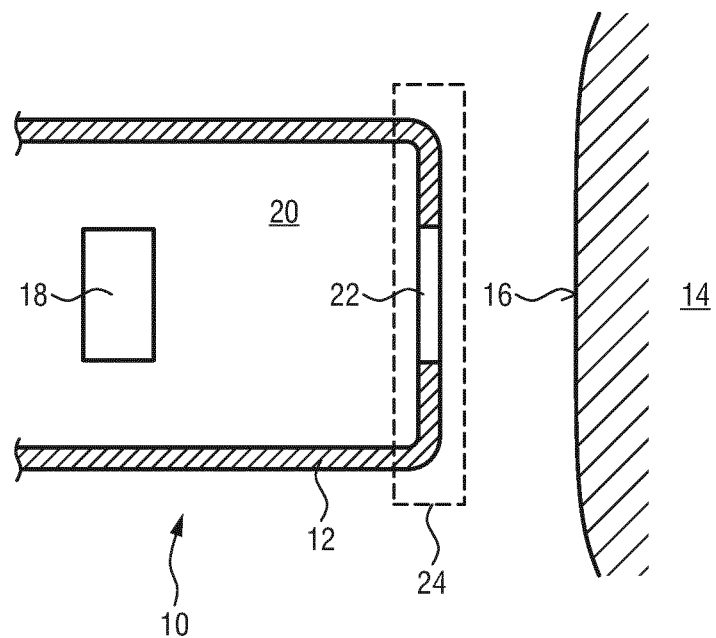
FIG. 1 shows a schematic representation of a skin parameter measurement device according to the prior art.

FIG. 1 shows a schematic representation of a skin parameter measurement device 10 according to the prior art. The skin parameter measurement device 10 comprises a housing structure 12 which is hollow and defines an interior cavity 20 for holding an optical sensing unit 18 configured to perform optical measurement of a skin parameter. The optical sensing unit 18 may comprise a camera platform adapted to measure skin oiliness, skin texture and pores. The housing structure 12 has a skin contact end 24 which is the end of the housing structure 12 when the skin parameter measurement device 10 is held in a position to perform skin parameter measurements on a skin surface 16 of a body part 14 (e.g. of a person). At the skin contact end 24, an opening 22 is formed for transmission of light signals sent from and/or received by the optical sensing unit 18 during the optical skin parameter measurements. The opening 22 functions therefore as a measurement window.

Figure 2:
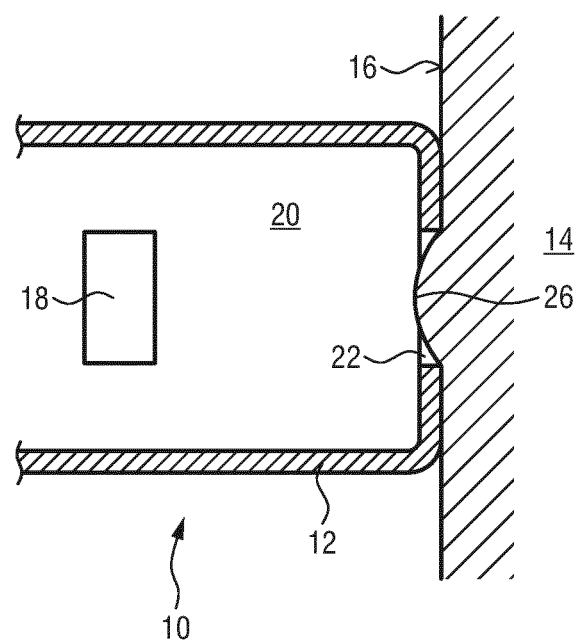
FIG. 2 shows a schematic representation of the skin parameter measurement device of FIG. 1 when the device is pressed against a skin surface.

The device known from the prior art suffers, however from variation in measurement results, when the same spot on the skin surface of the same person is measured repeatedly even without delays between measurements. One of the primary causes for such a variation is skin doming 26, i.e. the dome-like deformation of the skin surface that occurs when the housing structure 12 of the skin parameter measurement device 10 presses against elastic skin during skin parameter measurements. The housing structure 12 forms a rigid frame which, when pressed against the skin surface, causes the elastic skin to become convex. The effect of skin doming is illustratively shown in FIG. 2.

This skin doming phenomenon increases the variation of skin parameter measurement results in two ways. Firstly, it changes the visual properties of the skin being captured by the optical sensing unit (e.g. an illumination source and a camera). Through the measurement window 22 of the skin parameter measurement device 10, the illumination source (e.g. special LEDs) illuminates an otherwise unlit (hence darkened) skin surface so that the camera "sees" the illuminated skin surface. The skin doming leads to a change in the visual properties captured by the camera since the specifically positioned LEDs that are used to illuminate the skin surface at desired angles may be reflected differently at the point of incidence of the light rays due to the difference in the skin curvature. Secondly, skin doming can lead to skin not being caught in focus by the camera if the height of the skin dome exceeds that of the depth of field (DOF) of the camera. A more or less blurry picture results in the wrong measurement when the captured image is processed using image processing algorithms of the camera.

The effect of skin doming may be even affected in its extent and properties by a number of factors including natural skin properties (e.g. of a person) such as the elasticity, properties of the supporting tissues beneath the skin (e.g. muscle, bone), the design and/or dimensions of the rigid housing frame that is pushed against the skin surface for skin parameter measurement, and the pressure level and force with which the rigid housing frame is pushed.

While the first two factors are fixed for a given device and a given person whose skin parameter is to be measured, the pressure level and force has the largest effect on the skin doming and thus the variations of skin parameter measurement results. The force, with which the skin parameter measurement device is pressed against the skin may strongly vary, leading to variations of skin doming. For instance, a volunteer test shows that the range of forces applied by a group of test persons when asked to "make contact gently on the forehead or cheek" can be as large as from zero to 15 N.

Figure 3:
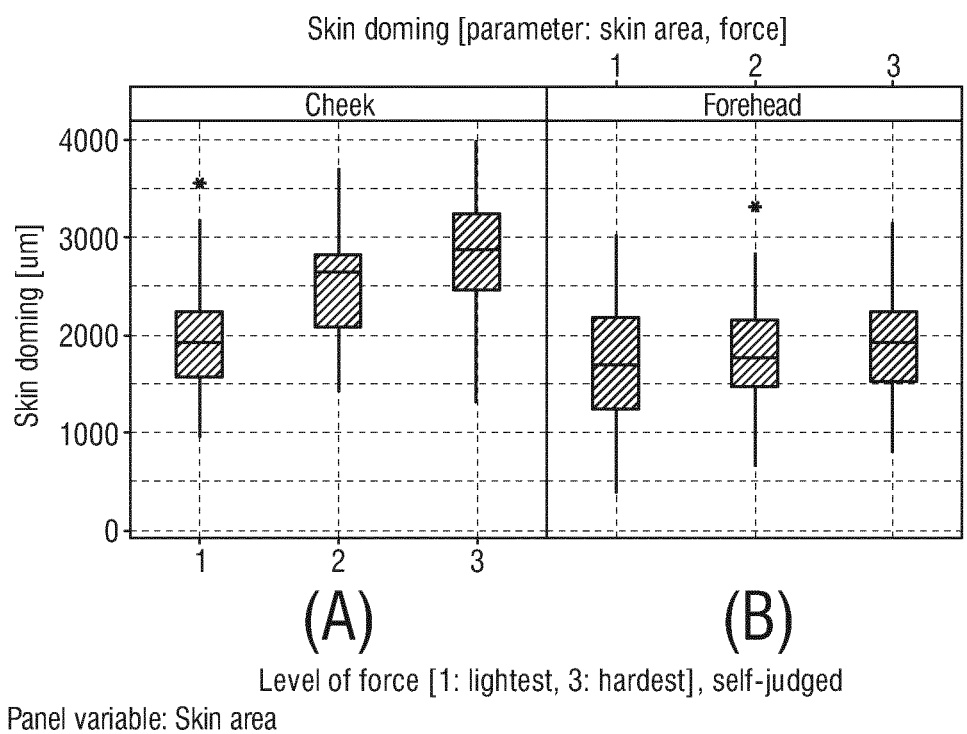
FIG. 3 shows a diagram representing results of a test regarding skin doming effect in response to pressing forces.

FIG. 3A-B show a diagram representing results of a test aimed at finding out how the force applied can lead to higher doming. The level of forces applied in the test ranges from 0.8 N to 15 N and is grouped into three levels: level 1 for the lightest force, level 2 for the intermediate force and level 3 for the strongest force. FIG. 3A refers to the test carried out on a cheek skin while FIG. 3B refers to the test carried out on a forehead skin. It is shown in this test that for forces in the range applied, the height of skin doming can ranges from 1 mm to 3 mm for a fixed window frame (i.e. the frame of window or opening brought into contact with the skin surface for skin parameter measurement) with a diameter of 15 mm, giving rise to a skin doming variation of 2 mm.

Skin parameter measurement devices known from the prior art have particular disadvantages that hamper the analysis of certain skin parameters (e.g. skin oiliness) that needs undisturbed reflection of light on the skin surface. Solutions that have been suggested in the art for preventing out-of-focus images include autofocus camera. However, besides the undesired cost uplift, such solutions fail to solve the problem that with strongly varying skin doming effects, the reflection of the emitted light also strongly varies, which even increases the variation of the measured parameter (e.g. value of skin oiliness).

Another solution known from the art suggests utilizing a glass plate or mesh in the focal plane of the camera in order to flatten skin doming. However, this measure strongly influences light reflection on the skin surface so that it is not suitable for measuring certain skin parameters such as skin oiliness.

A solution for measuring skin parameters is desirable which enables improved controlling of the skin doming effect without changing the reflection properties of the skin surface.

Figure 4:
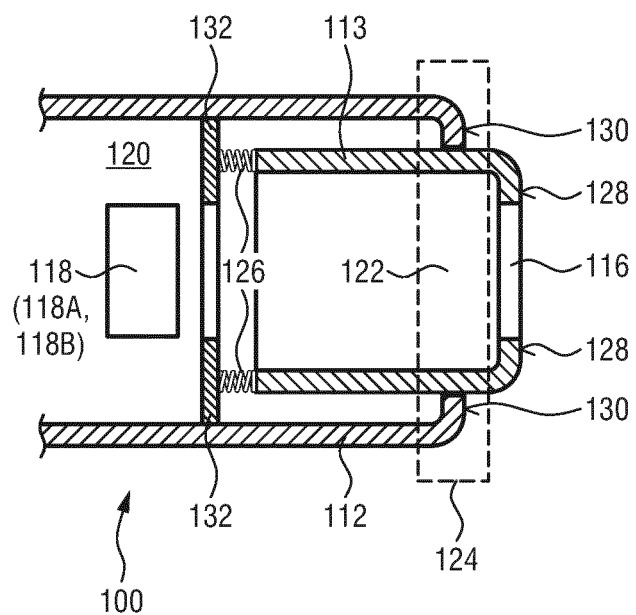
FIG. 4 shows a schematic representation of a skin parameter measurement device according to an embodiment of the present invention.

A schematic representation of a skin parameter measurement device 100 according to an embodiment of the present invention which solves the above-mentioned problems associated with the skin parameter measurement devices known from the art is schematically shown in FIG. 4. The skin parameter measurement device 100 comprises a housing structure 112 defining an interior cavity 120 for holding an optical sensing unit 118. The optical sensing unit 118 comprises an illuminating unit 118A and an imaging unit 118B. The optical sensing unit 118 is configured to perform optical measurement of a skin parameter such as skin oiliness, texture, pores and pigmentation. When the device 100 is in contact with a skin surface, the illuminating unit 118A illuminates the skin surface by emitting light through a first opening 122 at a skin contact end 124 of the housing structure 112. The emitted light is reflected on the illuminated skin surface and received by the imaging unit 118B.

The skin parameter measurement device 100 further comprises a movable part 113 that is connected to the housing structure 112 via an elastic connecting arrangement. The movable part 113 comprises a hollow inner space and a second opening 116 at the skin contact end 124. The elastic connecting arrangement is exemplarily shown as two springs 126 in FIG. 4. One side of the springs 126 is fixed to an end of the movable part 113 opposite to the second opening 116, while another side of the springs 126 is fixed to a board element 132 that protrudes the inner wall of the housing structure 112.

When no external force is applied to the skin parameter measurement device 100 (i.e. to press it against a skin surface), the skin parameter measurement device 100 is in an unpressed state, in which the movable part 113 protrudes the housing structure 112 at the skin contact end 124. As seen in FIG. 4, due to the elasticity of the springs 126, a front end section of the movable part 113 defining the second opening 116 is outside of the interior cavity 120 of the housing structure 112. The front end section has an end interface 128 which is preferably formed with a ring shape, e.g. a circular, rectangular or triangular ring shape. A base surface 130 of the skin contact end 124 of the housing structure 112 defining the first opening 122 is preferably formed with a ring shape.

Figure 5A:
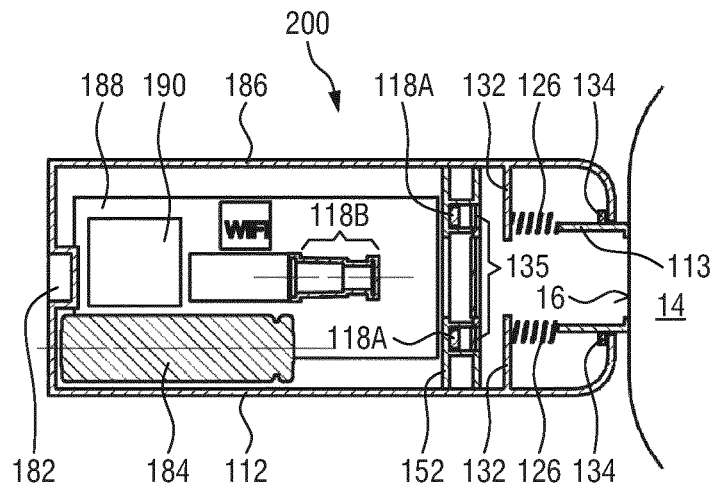
FIG. 5A-C show a schematic representation of a skin parameter measurement device according to another embodiment of the present invention in three different operational states.
Figure 5B:
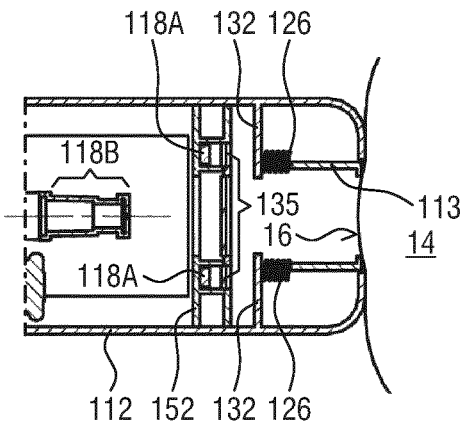
Figure 5C:
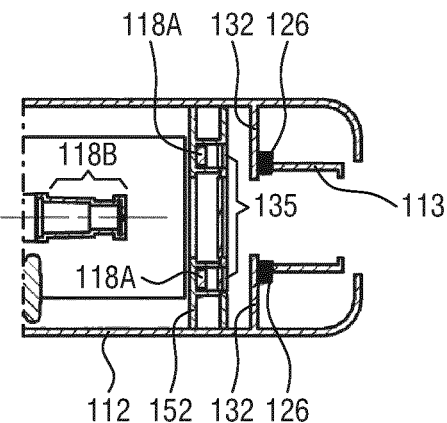

Due to the elasticity of the springs 126, the movable part 113 can move inwardly further into the interior cavity 120 of the housing structure 112 when it is brought into contact with a skin surface and pressed further against the skin surface. Thus, the movable part 113 functions as a "floating frame" surrounded by the housing structure 112 which functions as a "rigid frame". This will be shown in more details in FIG. 5A-C. FIG. 5A-C show a schematic representation of a skin parameter measurement device 200 according to another embodiment of the present invention. The skin parameter measurement device of FIG. 5A-C is similar to that of FIG. 4 (the same reference signs represent the same features in both set of figures). In the embodiment of FIG. 5A-C, the illuminating unit 118A of the optical sensing unit 118 comprises exemplarily a plurality of LEDs positioned to surround the imaging unit 118B comprising a camera. The plurality of LEDs are arranged on an illumination circuit board 152, preferably a printed circuit board (PCB). Further preferably, a polarizer unit 135 is provided at a side of the PCB facing the movable part 113. The springs 126 are preferably pretensioned contraction springs so that the movable part 113 experiences an outward contraction force.

In order to prevent the movable part 113 from moving further towards the outside of the housing structure 112 due to the spring forces, the movable part 113 comprises an abutting element 134 which is pressed against an edge of the skin contact end 124 of the housing structure 112, when no external force is applied to move the movable part 113 inwardly with respect to the housing structure 112.

Within the housing structure 112, a main circuit board 188 (e.g. a main PCB connected to power supply such as a battery), a battery case for receiving a battery 184 and/or a wireless connection port 186 may be arranged. At the end of the housing structure 112 opposite to the skin contact end of the housing structure 112, a charger socket 182 may be provided for charging the power supply of the device (e.g. the battery 184). Other functional units such as a storage unit 190 may be additionally integrated into the housing structure 112.

When the user puts the device 200 onto his/her skin, so that the movable part 113 (floating frame) just comes into contact with the skin surface 16 of a body part 14, the movable part 113 moves minimally inwards with respect to the housing structure 112 due to the slightest forces acting on the end interface of the movable part 113. This state of application is schematically shown in FIG. 5A. The minimum forces can be felt by the user holding the skin parameter measurement device 200 so that the user is advantageously provided with the cue to continue pressing.

When the device 200 is pressed further against the skin surface 16, the movable part 113 continues to move inwardly with respect to the housing structure 112 for a distance (e.g. 1-3 mm) until the housing structure 112 (external rigid frame) just makes contact with the skin, giving the user a feedback to stop further pressing. This state of application is schematically shown in FIG. 5B, which is also the state in which skin parameter measurements can be performed (i.e. "use position"). The feedback mechanism reduces the probability that a user presses the device exceptionally hard against the skin surface.

In FIG. 5C, the skin parameter measurement device 200 is in a state where the movable part 113 is pressed inwardly with respect to the housing structure 112 so that the springs 126 are maximally compressed to reach its innermost position within the interior cavity 120. This application state of the skin parameter measurement device 200 is normally not reached in actual use since the maximum doming height expected on skin surfaces of body parts such as forehead and cheek is smaller than the maximum distance the movable part 113 is allowed to move inwardly after reaching the state of FIG. 5B.

The present invention is advantageous regarding controlling of the pressure force acting on the skin surface of the user. The force with which the device is pressed against the skin of the user is not characterized by how the pressing force applied externally to the device, but by the compression force of the springs 126 at a given relative position between the movable part 113 and the housing structure 112 (such as shown in FIG. 5B). By properly choosing the parameters of a spring for the application (such as spring length and stiffness/spring constant), the spring compression force can be controlled so that it has no or minimal variation.

Hence, the resulting skin doming height is reduced compared to using a device without such a floating frame mechanism (e.g. FIG. 1). The lowered doming profile also facilitates to acquire skin images in focus for different users even using a camera as the imaging unit whose depth of field is less than 2.5 mm. In addition, the reduced skin doming effect also reduces the variation in visual skin properties occurring when different users press the device to their skin differently for skin parameter measurement and even when the same user presses differently in different measurement occasions. Thus, the present invention achieves skin parameter measurements results with less variation leading to higher reliability in skin analysis.

An additional advantage of the present invention is that the motion of the skin parameter measurement device (e.g. the motion of the housing structure 112 between the states shown in FIG. 5A and FIG. 5B) is essentially a linear motion perpendicular to the skin surface. This means that not only the strength of the pressure force but also its direction with respect to the skin surface is better controllable, leading to less variation in skin doming.

Still a further advantage of the present invention is related to the fact that a first frame (i.e. the movable part as the floating frame) and then a second frame (i.e. the housing structure as the rigid frame) come in contact with the skin surface before performing the measurement. This improves the feedback to the user compared to a device with a rigid measurement window frame (e.g. FIG. 1), since the probability of incorrectly angled placement of the device with respect to the skin surface of the user is decreased.

Figures 6A, 6B:
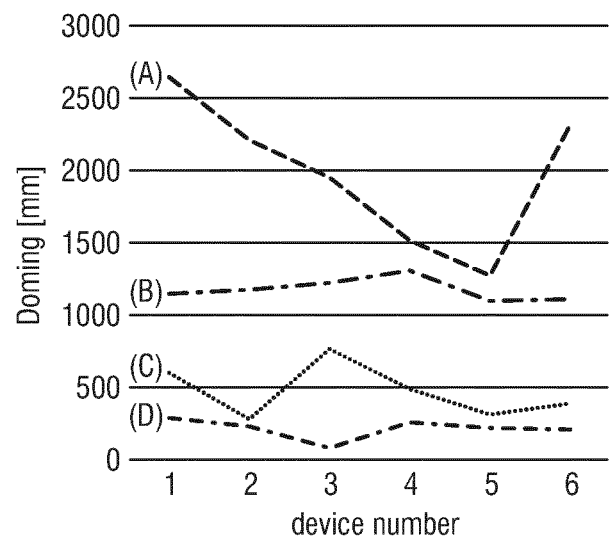
FIG. 6A shows a diagram representing results of a test regarding skin doming effect with various spring pretensions and designs.
FIG. 6B shows a table representing design parameters for a plurality of skin parameter measurement device embodiments.
Figure 6C:
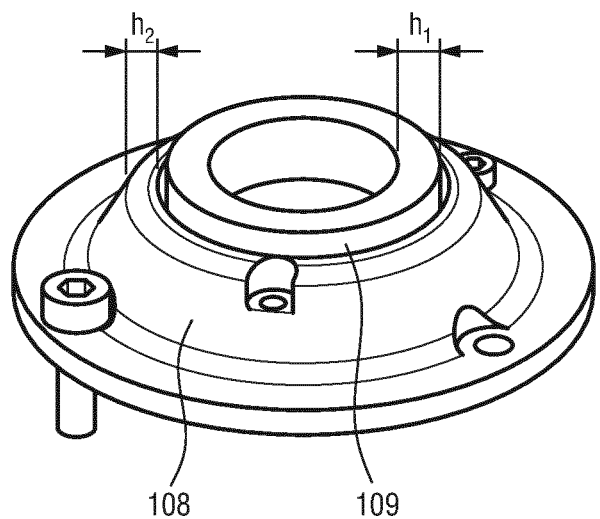
FIG. 6C shows an exemplary design of a skin end portion of the housing structure and the movable part.

FIG. 6A shows a diagram representing results of a test regarding skin doming effect with various spring pretensions and device designs. The curves A, B, C, D represent each a measurement of skin doming height (vertical axis) under a different configuration of spring pretension (0.8 N or 1.5 N, respectively) and skin surface applied (cheek or forehead, respectively) for a plurality of devices enumerated from 1 to 6 (horizontal axis). The device design parameters "floating rim thickness", "floating rim shape" and "fixed rim thickness" are shown in FIG. 6B. The "floating rim thickness" and "floating rim shape" refer to the width of the front end section interface of the movable part and its geometric form, i.e. of the ring shape being either round (circular) or flat (rectangle). The "fixed rim thickness" refers to the width of the base surface of the skin contact end of the housing structure. FIG. 6C shows an exemplary design: the floating rim thickness of the circular movable part 109 (floating rim)

is indicated by $h_1$, the fixed rim thickness of the housing structure 108 (fixed rim) is indicated by $h_2$.

The test shows that the pretension of 0.8 N achieves the better result in terms of both skin dome height and skin doming variation. Further, using springs with a pretension of 0.8 N, the skin doming height ranges from 1.5 mm to 2.3 mm when the skin parameter measurement device is pressed against the skin surface by a force ranging from 0.8 N to 15 N, giving a skin doming variation of 0.8 N. This skin doming variation is significantly lowered compared to the value (2 mm) provided by a device of the prior art (FIG. 3A-B).

Figure 7A:
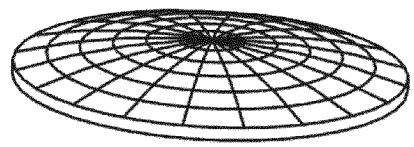
FIG. 7A-B show a diagram representing results of a comparison measurement regarding two designs for the movable part of a skin parameter measurement device according to two further embodiments of the present invention.
Figure 7B:
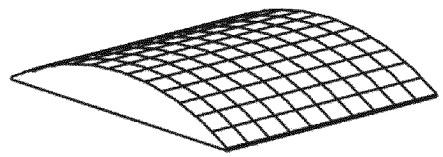

FIG. 7A-B show a diagram representing results of a comparison measurement using two designs regarding the measurement window frame (i.e. the frame of the second opening defining a measurement window) of movable part. In FIG. 7A, measurement result for a circular measurement window frame is shown, wherein the diameter of the window frame is 15 mm and the device is pressed with low pressure against a skin surface of a forehead. Also, the measurement result of FIG. 7A has been obtained without pressure control, i.e. using a rigid measurement window frame without suspension to limit pressing forces. In FIG. 7B, measurement result for a rectangular measurement window frame is shown, wherein the dimension of the window frame is 9.5 mm×12.4 mm and the device is pressed with low pressure (in particular, the pressing force is between 1 N and 2 N) against a skin surface of a forehead. The comparison measurement shows that, compared to the rectangular measurement window frame, a circular measurement window frame better homogenizes skin doming in all directions and minimizes the influence of the orientation, i.e. in which the device is held or placed onto the skin surface, upon skin doming.

A (circular) measurement window frame that is of the same dimension as or larger dimension than the rectangular Field of View (FOV) of the camera used as the imaging unit is preferable to get an unobstructed image. In particular, the FOV of the camera is defined by the angle of view of the camera and its distance to the focal plane. Hence, the size of the measurement window frame can be chosen based on these two parameters of the camera. The window frame has further preferably a dimension of 12 mm×9 mm or larger.

Figure 8:
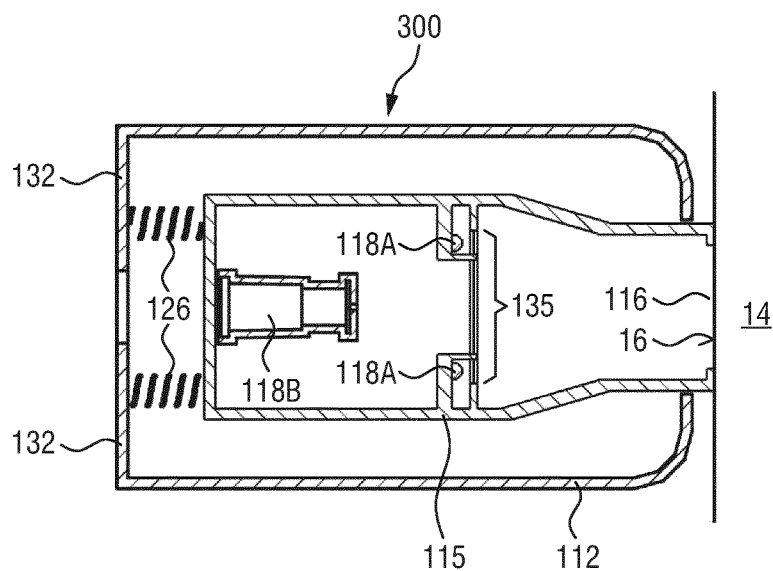
FIG. 8 shows a schematic representation of a skin parameter measurement device according to still a further embodiment of the present invention.

FIG. 8 shows a schematic representation of a skin parameter measurement device 300 according to still a further embodiment of the present invention which differs from the embodiment shown in FIG. 5A-C in that the optical sensing unit 118 is fixedly arranged within the movable part 115. As exemplarily shown in FIG. 8, the illuminating unit 118A and the imaging unit 118B (e.g. a camera) of the optical sensing unit 118 are fixedly included in a back end section of the movable part 115 which is the opposite end to the front end section defining the skin end interface and the second opening 116. Advantageously, the field of focus of the camera is defined with respect to the ring-shaped skin end interface which forms a skin contacting ring, regardless of the relative position of the spring-loaded floating frame (i.e. the movable part 115) with respect to the external rigid frame (i.e. the housing structure 112). To assure a controlled skin doming in this situation, the springs have preferably a low or zero stiffness (e.g. between 0 and 0.5 N/mm) and/or a defined pretension (e.g. 0.8 N).

Preferably, the back end section of the movable part 115 has a larger cross section than the back end section, so that the optical sensing unit can be securely included in the movable part 115. This is, however, not limiting the present invention and other forms with varying or constant diameter (such as cylindrical) may be used for the movable part.

In the following, further embodiments of the skin parameter measurement device are described which, in addition to the features included by the embodiments described above (i.e. FIG. 4, 5A-C, 8), further comprises an electrical sensing unit for measuring a second skin parameter, preferably a skin impedance, wherein the electrical sensing unit is further preferably arranged at a front end section of the movable part defining the second opening. The features described in FIG. 1-8 are, however, independently applicable to the further embodiments below and vice versa.

Bio-impedance can be measured by placing two or more electrical contacts, which have a fixed distance from each other, or an array of electrical contacts, onto the skin surface. An electrical signal, preferably a harmonic signal (e.g. an electrical signal comprising one or more harmonics), is sent through the electrodes, where the differences in amplitude and phase between the input signal and received signal are measured. This can be particularly utilized to measure the skin impedance, which can be an indicator of multiple skin properties, for instance the water content (hydration), the sebum content and/or the salt content (e.g. in terms of percentage).

To a certain degree, the distance between the electrical contacts (i.e. electrodes) and the signal frequency determine the depth of the skin at which the impedance can be measured. They also determine the effect of a certain skin parameter, such as hydration, on the measured skin impedance.

A stable contact between the skin surface and the electrodes is advantageous for obtaining reliable results in skin impedance measurements. As skin may have a plurality of flexible textures, the variation in contact pressure leads to variation in the form and size of the contact interface between the skin surface and the skin parameter measurement device. This leads to variations of the measurement results. Causes of contact pressure variations are typically the force the operator uses when pressing the skin parameter measurement device to the skin surface, but also the angle with which the device is held with respect to the skin surface when it is being pressed against the skin. Any angle deviating from a perpendicular angle with respect to the skin surface may cause differences in the pressure distribution and thus variation in the measured skin impedance. Finally, these effects are larger for electrical contacts with a smaller contact area (i.e. the area of the skin surface contacted by the electrical contacts) than those with a larger contact area.

Figure 9:
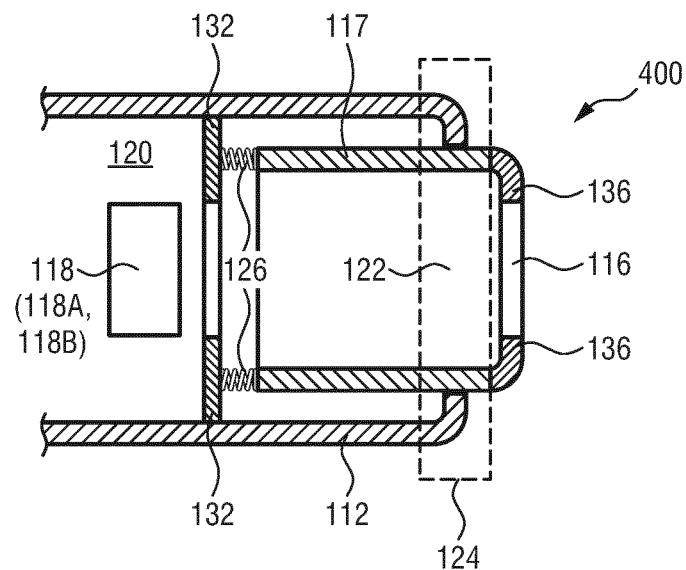
FIG. 9 shows a schematic representation of a skin parameter measurement device according to still a further embodiment of the present invention.

FIG. 9 shows a skin parameter measurement device 400 according to an embodiment of the present invention. The skin parameter measurement device 400 comprises essentially the same features as the embodiment shown in FIG. 4 and, in addition, an electrical sensing unit which preferably comprises two electrical contacts 136 formed at the movable part 117. Exemplarily, the electrical contacts 136 are provided at the front end section of the movable part 117 to extend inwardly from the skin end interface of the movable part 117. Alternatively or additionally, the electrical contacts 136 may extend inwardly along the movable part 117 all through its entire length or over a section of the entire length.

The present invention thus provides a combination of an optical measurement device and an electrical measurement device, so that the applicability of the skin parameter measurement device is larger compared to devices known from the art.

In FIG. 9, two electrical contacts are exemplarily shown. However, the number of electrical contacts may be more than two. As mentioned above, the front end section of the movable part 117 may be formed in a ring shape, preferably a circular, rectangular or triangular ring shape. Further preferably, the electrical sensing unit 136 comprises a plurality of electrical contacts fixedly separated from each other and distributed within the ring shape of the front end section of the movable part 117.

In this way, angular variations during handling of the skin parameter measurement device by the user is minimized. Preferably, the "diameter" of the ring shape (i.e. the maximum, average or minimum distance between two opposite sides of the ring shape, in particular at the outer or inner circumference of the ring shape) is sufficiently large to ensure proper feedback of correct placement to the user when the device is placed on the skin. For instance, the diameter may range from 10 mm to 50 mm, more preferably between 15 mm and 20 mm.

Figure 10:
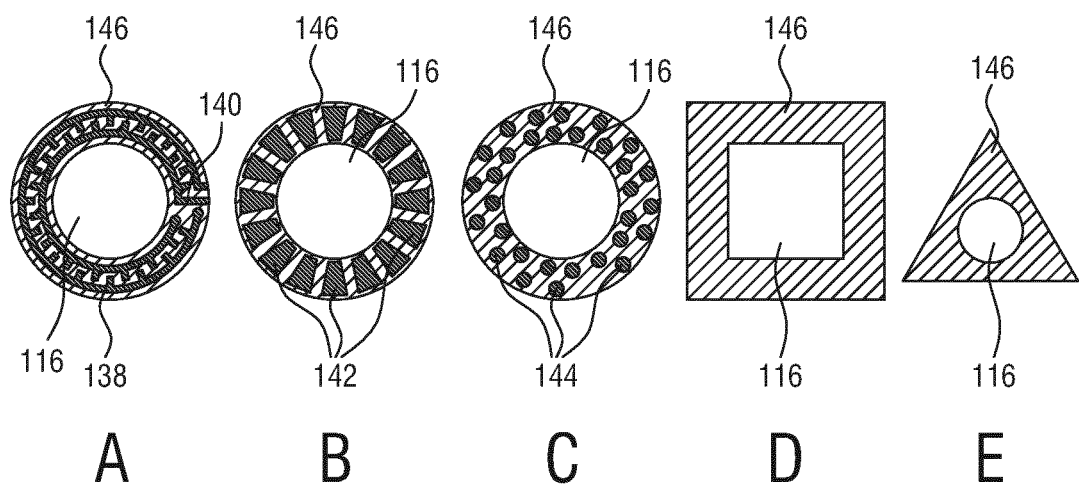
FIG. 10A-E show a schematic representation of a plurality of designs for the front end section of the movable part and the base surface of the housing structure of a skin parameter measurement device according to still further embodiments of the present invention.

FIG. 10A-C show a plurality of exemplary electrical contacts distributed over a circular ring shape of the movable part. In FIG. 10A, two electrical contacts 138, 140 are provided within the base surface 146 of the front end section of the movable part, wherein the electrical contacts 138, 140 each comprise a plurality of tooth parts. In FIG. 10B, electrical contacts 142 are circularly distributed over the base surface 146, while each electrical contact 142 has a trapezoidal form. In FIG. 10C, circular electrical contacts 144 are circularly distributed over the base surface 146.

FIG. 10D-E show each an exemplary form of the base surface 146 of the movable part defining the second opening 116. In FIG. 10D, the base surface 146 has a rectangular ring shape at its both circumferences, while the base surface 146 in FIG. 10E has a triangular ring shape at its outer circumference and a circular ring shape at its inner circumference.

In addition to that, the elastic connecting arrangement (shown exemplarily as two springs 126 in FIG. 9) enables that the floating frame (i.e. the movable part 117) can move back and forth in a rigid frame (i.e. the housing structure 112). Preferably, the skin contact end of the housing structure comprises a ring-shaped base surface for contacting with the skin surface, the ring-shaped base surface having a ring width of 2 mm or larger. This ensures a stable base for skin contact at the moment the floating frame is fully levelled with the base surface when the measurement tool is pressed to the skin surface.

Figure 11:
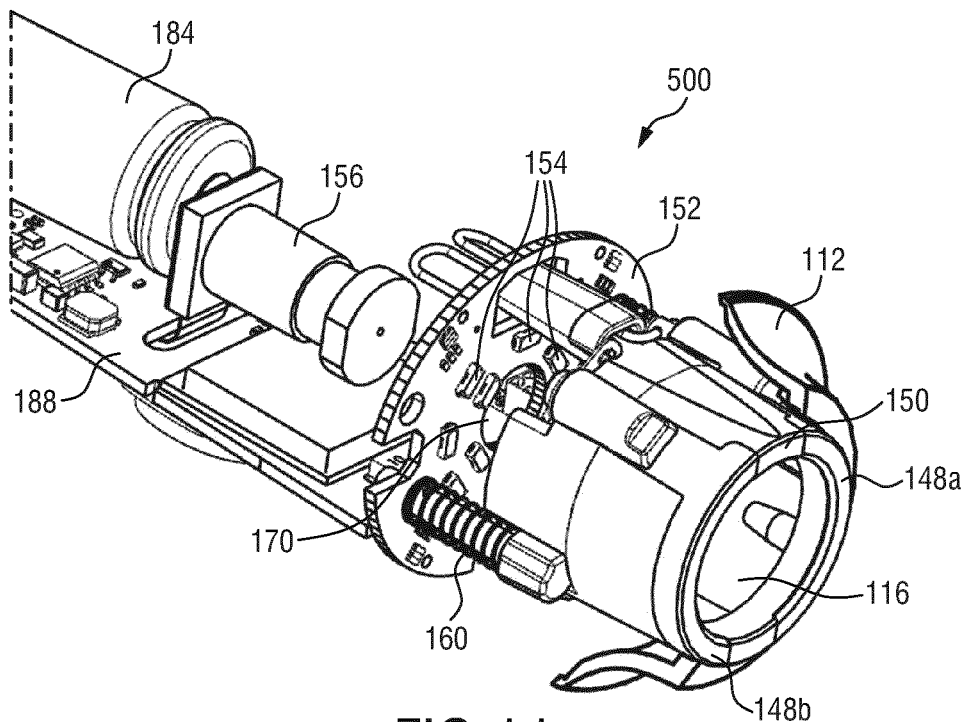
FIG. 11 shows a schematic representation of a skin parameter measurement device according to still a further embodiment of the present invention.

FIG. 11 shows a skin parameter measurement device 500 according to a further embodiment of the present invention. Here, the movable part 150 has a circular ring form at its front end section. Two electrical contacts 148a, b are arranged within the ring form so that they form a part of the movable part 150. In particular, the electrical contacts 148a,b have each an arc-form, separated by two sections of the movable part 150. The housing structure 112 is provided to surround the movable part 150. A illumination circuit board 152, preferably a printed circuit board (PCB), is fixedly arranged within the interior cavity of the housing structure 112, wherein a plurality of LEDs 154 (illumination unit) are circumferentially arranged around a central hole 170 of the illumination circuit board 152. A camera 156 (imaging unit) is arranged inwards with respect to the illumination circuit board 152 within the interior cavity of the housing structure 112. The light emitted by the LEDs 154 travels to the skin surface via the second opening 116 of the movable part 150 when the device 500 is brought to proximity or in contact with the skin surface. The light reflected from the skin surface then travels to the camera 156 via the central hole 170 of the illumination circuit board 152.

Figures 12A, 12B:
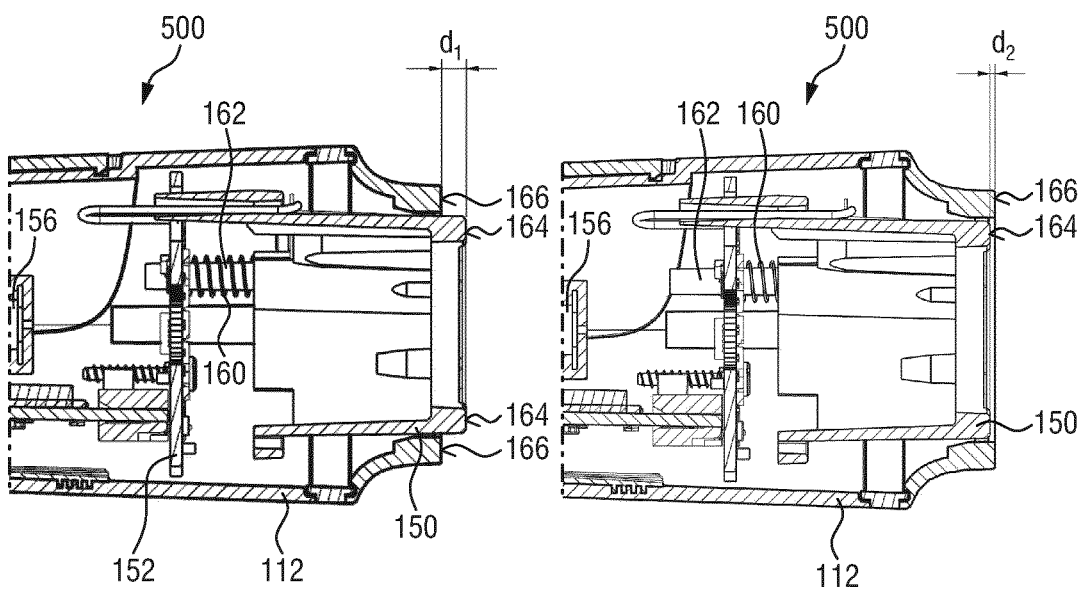
FIG. 12A-B show a schematic representation of the skin parameter measurement device according to the embodiment of FIG. 11 in cross-sectional view for two operational states.

In FIG. 12A-B, the device 500 of FIG. 11 is shown in a side view. In FIG. 12A, the device 500 is in an unpressed state, while in FIG. 12B, the device 500 is brought into contact with a skin surface (not shown) and the movable part 150 moves inwardly due to skin doming (not shown).

The movable part 150 (floating frame) comprises preferably a first portion made of plastic and a second portion which forms the electrical contacts 148a,b. The first portion consists of two guiding legs 162 which carry the springs 160 and which extend to go through the illumination circuit board 152 via two guiding holes formed therein. This ensures a balanced linear motion for the device 500 during use. The natural length of the springs 160 is exemplarily 18.7 mm, while in the default unpressed state, they are contracted by 7.4 mm, giving a pretension of 0.55 N.

Normally, when the user pressed the skin analyst to his/her head, the skin end interface 164 of the movable part 150 (floating frame) is brought into contact with the skin surface (FIG. 12A). From this position on, the floating frame further pressed against the skin surface can move inwardly by a distance of 2.5 mm (shown as $d_1$ in FIG. 12A) until the base surface 166 of the housing structure (outer static frame or rigid frame) touches the skin surface of the user. Given the convex curvature of the skin surface of body parts such as the forehead or the cheek, the distance of the skin end interface 164 of the movable part 150 from the base surface 166 of the housing structure 112 that touches the skin surface (shown as $d_2$ in FIG. 12B) in this final position is 1 mm. At this point, the calculated spring force due to compression is 0.81 N. For small expected variations in the length of the compressed spring of between +0.5 mm and −0.5 mm (the signs + and − refer to the increase and decrease of the spring length, respectively), the variation in spring force will be within the range between +0.02 N and −0.02 N (the signs + and − refer to the direction of the spring force when the length is decreased and increased, respectively). Thus, the variation in spring force is at an advantageously low level.

The camera 156 used in the current embodiment has a depth of field of +/−1.5 mm. Further, the camera 156 has a focal plane which is 0.5 mm inwards from the ideal final position of the skin end interface 164 of the floating frame. This is to account for the average level of skin doming that occurs due to the pressure being exerted by the floating frame onto the skin surface because of the springs 162. This inward bias of the focal plane is due to the fact that skin domes only in one direction due to both natural curvature (on forehead and cheek) and due to the effect of pressure.

In further embodiments, the floating frame may be supported using means other than guiding legs and the springs may be guided using other means for positioning. When guiding legs are utilized, any or all of the legs may provide an extra functional channeling (e.g. tunnels) for carry wires from the skin contact end of the device to the interior cavity, even to the end of the device opposite to the skin contact end. Additionally, any number of or all legs may be used for bearing the springs with additional guiding rails or other mechanisms to create a balanced spring loaded floating system. The forces may also be adjusted to suit different users and/or different applications if different parts of the body are to be measured and/or the overall dimensions of the framing of the image are different.

In order to ensure that images are only taken when the floating frame is sufficiently moved inwards (e.g. by a predefined distance) to allow contact between the external rigid frame and the skin surface, thus making sure that the skin is in the focal area of the camera, a first detection unit is preferably added to detect the relative position of the floating frame with respect to the external rigid frame. That detection can be preferably used as a trigger for taking an image by the camera.

The present invention may be configured to signal that a skin impedance measurement is correctly performed when a proper contact between the electrical contacts and the skin is detected. For instance, this may be achieved by a second detection unit for checking the impedance readings of the device with respect to a lower threshold. Skin has normally a specific impedance range. At a frequency of 32 kHz for the applied electrical signal, the specific impedance range is 4 to 45 KOhm for an average person. In case of a standalone device with a user interface (UI), when a pre-defined time duration has lapsed after pressing a "measure" button, the device can indicate via the UI that a correct measurement has been acquired if a value above the lower threshold has been detected within the pre-defined time duration, or the opposite if no value above the lower threshold has been detected within that duration. In case of a "connected device, a user can start a measurement for instance via a smart phone app. If, after a pre-defined time duration measured from start of measurement, no value above the lower threshold is acquired, the user can receive a message (e.g. via the app) that the measurement was incorrect and should be redone.

In order to ensure the correct pressure level during the impedance measurement, a third detection unit may be added to detect the relative position of the electrodes with respect to the fixed outer frame. The impedance measurement is performed only when a predefined relative position along the longitudinal direction of the fixed outer frame is detected. This detection can be used as a trigger for acquiring an impedance reading at the moment the springs are sufficiently compressed.

Figure 13:
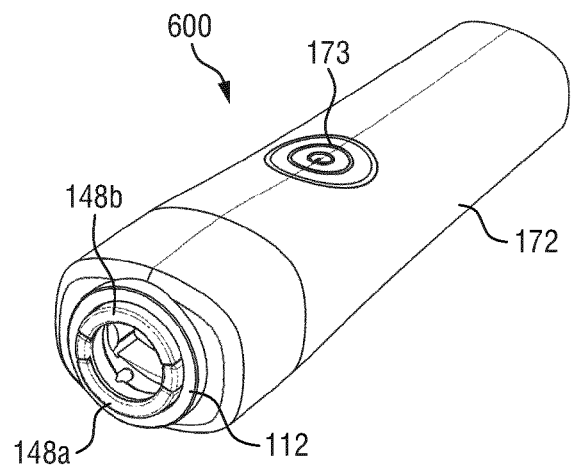
FIG. 13 shows a schematic representation of a skin parameter measurement device according to still a further embodiment of the present invention.

FIG. 13 shows a schematic representation of a skin parameter measurement device 600 according to still a further embodiment of the present invention. In this embodiment, the housing structure 112 of the skin parameter measurement device 600 comprises a removable section 172. A button 173 for powering on and/or off the device 600 is preferably arranged on a side of the housing structure 112.

Figure 14A:
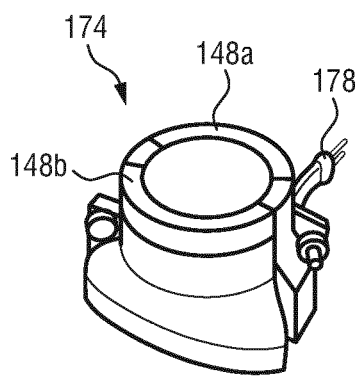
FIG. 14A-B show each a schematic representation of a skin parameter measurement device according to still a further embodiment of the present invention.
Figure 14B:
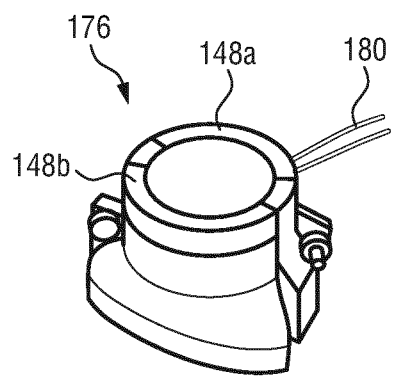

FIG. 14A-B show each a schematic representation of a movable part of the present invention. The movable part 174, 176 shown in FIG. 14A-B comprises two electric contacts 148a,b each having an arc-form and separated by a plastic portion of the movable part 174, 176. The electrical contacts 148a,b are supported by the plastic portion of the movable part 174, 176. Further, a plug 178 or wirings 180 are provided for the movable part 174, 176 of the two examples, respectively, e.g. for connecting with the illumination circuit board and/or the main power supply circuit board (main PCB) of the device. The movable parts 174, 176 may be attached to a housing structure (e.g. via means for detachable mechanical connections such as clips) to form the skin parameter measurement device.

The combination of ring-shaped electrodes having a sufficient diameter with spring suspension in rigid frame with a sufficient, preferably flat base surface is advantageous to achieve a device which provides feedback to the user as described above when it is stably placed on the skin surface. Further, in the stably placed position, pressure-induced variation on the impedance measurement is reduced to a acceptably low level, resulting in sufficiently low measurement variation.

The combination of the spring-suspended ring-shaped electrodes with the optical sensing functionality achieves an integral solution where both the contact pressure for electrical skin parameter measurements (e.g. skin impedance measurement) and the skin doming for optical skin parameter measurements (e.g. skin imaging) are better controlled. Further advantages of this combined solution is a more compact and cost efficient design with optimal ergonomic properties.

Figure 15:
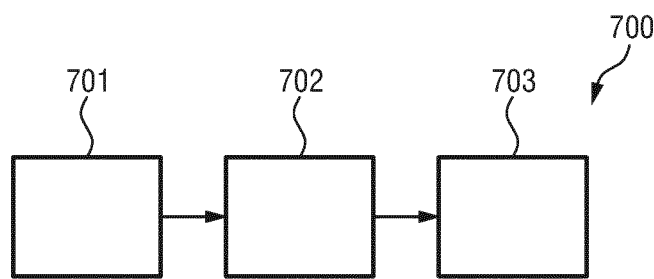
FIG. 15 shows a skincare system according to an embodiment of the present invention.

FIG. 15 shows a preferable skincare system 700 comprising a skin parameter measurement device 701, an analysis unit 702 for analyzing a skin parameter measurement result provided by the device 701 and an adaptation unit 703 for adapting a setting of the system based on an analysis result of the analysis unit 702. The skin parameter measurement device 701 can be any embodiment of the present invention described above.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for measuring at least one skin parameter of skin, the device comprising:
   a housing structure defining an interior cavity and a first opening at a skin contact end of the interior cavity;
   a movable part connected to the housing structure via an elastic connecting arrangement, the movable part being movable with respect to the housing structure such that the movable part at least partly remains within the housing structure and configured to protrude from the first opening when no external force is applied to the movable part, the movable part comprising a front end section for contacting a skin surface of the skin and a second opening through the front end section;
   an optical sensor for measuring a first skin parameter of the skin, the optical sensor being provided within the interior cavity of the housing structure and comprising an illuminating unit for illuminating the skin surface by emitting light through the second opening of the movable part and a camera, having a focal area, for acquiring an image of the skin based on light reflected by the illuminated skin surface;
   a plurality of electrical contacts for measuring a second skin parameter of the skin, wherein the plurality of electrical contacts are arranged on the front end section of the movable part around a perimeter of the second opening; and
   a trigger for detecting a relative position of the movable part with respect to the housing structure, and for triggering the measuring of the first skin parameter by the optical sensor when a predefined relative position is detected, wherein the predefined relative position ensures that the skin surface of the skin is in the focal area of the camera.

2. The device according to claim 1, wherein the front end section of the movable part is ring shaped.

3. The device according to claim 2, wherein the plurality of electrical contacts are separated from each other on the front end section of the movable part.

4. The device according to claim 2, wherein the plurality of electrical contacts comprise two electrical contacts, each of the electrical contacts being provided within one of two semi-ring sections of the front end section of the movable part.

5. The device according to claim 2, wherein the plurality of electrical contacts are distributed within the front end section of the movable part.

6. The device according to claim 1, wherein the illuminating unit is arranged on an illumination circuit board fixedly arranged within the housing structure.

7. The device according to claim 6, wherein the illumination circuit board comprises a ring form with a circuit board opening for transmission of the light to the camera.

8. The device according to claim 1, wherein the elastic connecting arrangement comprises at least one spring.

9. The device according to claim 8, wherein the movable part comprises at least one supporting element for carrying the at least one spring.

10. The device according to claim 1, wherein the elastic connecting arrangement comprises two springs.

11. The device according to claim 10, wherein each of the two springs comprises a pretensioned spring having a pretension of 0.55 N.

12. The device according to claim 1, wherein the illuminating unit and/or the camera are fixedly arranged within the movable part.

13. A skincare system, comprising:
the device as claimed in claim 1 for measuring the first and second skin parameters; and
an analysis unit for analyzing measurement results provided by the device.

14. The device according to claim 1, wherein the second skin parameter of the skin measured by the plurality of electrical contacts is impedance, the system further comprising:
a detector configured to check impedance values measured using the plurality of electrical contacts with respect to a lower threshold, and to indicate that the impedance values are invalid when no impedance value exceeds the lower threshold within a pre-defined time duration.

15. A method for measuring a skin parameter of skin using a device comprising a housing structure defining an interior cavity and a first opening at a skin contact end of the interior cavity; a movable part connected to the housing structure via an elastic connecting arrangement, the movable part being movable with respect to the housing structure such that the movable part at least partly remains within the housing structure and configured to protrude from the first opening when no external force is applied to the movable part, the movable part comprising a front end section for contacting a skin surface of the skin and a second opening through the front end section; an optical sensor provided within the interior cavity of the housing structure and comprising an illuminating unit and a camera having a focal area; and a plurality of electrical contacts arranged on the front end section of the movable part around a perimeter of the second opening, the method comprising:
detecting a relative position of the movable part with respect to the housing structure;
triggering measurement of a first skin parameter of the skin using the optical sensor when the detected relative position matches a predefined relative position, wherein the predefined relative position ensures that the skin surface of the skin is in the focal area of the camera;
illuminating, using the illuminating unit, the skin surface of the skin by emitting light through the second opening of the movable part;
acquiring, using the camera, an image of the skin from light reflected by the illuminated skin surface; and
performing, using the plurality of electrical contacts, measurement of a second skin parameter when the device is in contact with the skin surface.

16. A non-transitory computer readable medium storing program code that, when executed by a computer, cause the computer to carry out the method as claimed in claim 15.

17. A device for measuring at least one skin parameter of skin, the device comprising:
a housing structure defining an interior cavity and a first opening at a skin contact end of the interior cavity;
a movable part connected to the housing structure via at least one spring, wherein the movable part is movable within the housing structure and is configured to protrude from the first opening when no external force is applied to the movable part, wherein the movable part comprises a front end section for contacting a skin surface of the skin and a second opening through the front end section;
a plurality of LEDs provided within the interior cavity of the housing structure, and configured to illuminate the skin surface by emitting light through the second opening of the movable part;
a camera provided within the interior cavity of the housing structure, and configured to receive light reflected by the illuminated skin surface, responsive to the emitted light, through the second opening of the movable part to measure a first skin parameter of the skin;
a plurality of electrical contacts arranged on the front end section of the movable part around a perimeter of the second opening, and configured to measure a second skin parameter of the skin; and
a trigger configured to detect a relative position of the movable part with respect to the housing structure, and to trigger the measuring of the first skin parameter when a predefined relative position is detected, wherein the predefined relative position ensures that the skin is in a focal area of the camera when the housing structure is in contact with the skin surface.

18. The device according to claim 17, wherein the front end section of the movable part is ring shaped.

19. The device according to claim 18, wherein the plurality of electrical contacts are separated from each other on the front end section of the movable part.

20. The device according to claim 18, wherein the plurality of electrical contacts comprise two electrical contacts, each of the electrical contacts being provided within one of two semi-ring sections of the front end section of the movable part.

* * * * *